United States Patent
Montet et al.

(10) Patent No.: US 10,144,947 B2
(45) Date of Patent: Dec. 4, 2018

(54) METHOD FOR DETECTING, IDENTIFYING AND ENUMERATING MICRO-ORGANISMS IN A POROUS SUPPORT DRY-IMPREGNATED WITH A DEHYDRATED REACTION MEDIUM

(71) Applicant: BIOMÉRIEUX, Marcy l'Etoile (FR)

(72) Inventors: Marie-Pierre Montet, Venissieux (FR); Christine Rozand, St Genis les Ollières (FR)

(73) Assignee: BIOMERIEUX, Marcy l'Etoile (FR)

( * ) Notice: Subject to any disclaimer, the term of this patent is extended or adjusted under 35 U.S.C. 154(b) by 9 days.

(21) Appl. No.: 15/109,025

(22) PCT Filed: Jan. 8, 2015

(86) PCT No.: PCT/FR2015/050035
§ 371 (c)(1),
(2) Date: Jun. 29, 2016

(87) PCT Pub. No.: WO2015/104501
PCT Pub. Date: Jul. 16, 2015

(65) Prior Publication Data
US 2016/0326564 A1 Nov. 10, 2016

(30) Foreign Application Priority Data
Jan. 9, 2014 (FR) .................. 14 50149

(51) Int. Cl.
| C12Q 1/04 | (2006.01) |
| C12M 1/16 | (2006.01) |
| C12M 1/34 | (2006.01) |
| C12M 1/12 | (2006.01) |
| D06M 23/08 | (2006.01) |

(52) U.S. Cl.
CPC .............. C12Q 1/04 (2013.01); C12M 25/02 (2013.01); C12M 41/36 (2013.01); D06M 23/08 (2013.01)

(58) Field of Classification Search
None
See application file for complete search history.

(56) References Cited

U.S. PATENT DOCUMENTS

| 2009/0012425 A1* | 1/2009 | Dodge ............... A61B 10/0045 600/572 |
| 2011/0244511 A1* | 10/2011 | Mach ...................... C12Q 1/04 435/39 |
| 2013/0089887 A1 | 4/2013 | Gazenko |

FOREIGN PATENT DOCUMENTS

| FR | 2 268 076 A1 | 11/1975 | |
| WO | 03/093819 A1 | 11/2003 | |
| WO | 2005/038123 A1 | 4/2005 | |
| WO | WO 2005038123 A1 * | 4/2005 | ........... B29C 70/465 |
| WO | 2005/061013 A1 | 7/2005 | |
| WO | 2009/082667 A1 | 7/2009 | |

OTHER PUBLICATIONS

Fridley et al., "Controlled Release of Dry Reagents in Porous Media for Tunable Temporal and Spatial Distribution Upon Rehydration"., Lab on a Chip., vol. 12. No. 21, p. 4321, 2012.
Jorgensen et al., "Antimicrobial Susceptability Testing: A Review of General Principles and Contemporary Practices". Clinical Infectious Diseases, vol. 49, No. 11, pp. 1749-1755, 2009.
Zurita et al., Diagnosis and Susceptibility Teasting of Methicillin-resistant *Staphylococcus Aureus* in Latin America. The Brazilian Journal of Infectious Diseases, vol. 14, pp. 97-106, 2010.
May 18, 2015 Written Opinion issued in International Patent Application No. PCT/FR2015/050035.
May 18, 2015 International Search Report issued in International Patent Application No. PCT/FR2015/050035.

\* cited by examiner

*Primary Examiner* — Michelle F. Paguio Frising
(74) *Attorney, Agent, or Firm* — Oliff PLC (57) ABSTRACT

A method for the detection, identification and enumeration of microorganisms in a porous support including reaction medium powder throughout its thickness, the support having been dry-impregnated throughout its thickness by a dehydrated reaction medium. Further, a device is used and enables the method to be carried out.

21 Claims, 1 Drawing Sheet

METHOD FOR DETECTING, IDENTIFYING AND ENUMERATING MICRO-ORGANISMS IN A POROUS SUPPORT DRY-IMPREGNATED WITH A DEHYDRATED REACTION MEDIUM

FIELD

The present invention relates generally to the field of microbiological analysis. More particularly, it relates to a method for the detection, identification and/or enumeration of microorganisms in a porous support dry-impregnated throughout its thickness by a dehydrated reaction medium.

BACKGROUND

In the fields of clinical diagnostics and industrial microbiological control, food-processing, pharmaceuticals or cosmetics, gelled culture media in petri dishes, most frequently agar media, have been an indispensable tool in the detection and identification of pathogenic microorganisms since the end of the 19$^{th}$ century.

Several products have been made commercially available to replace a petri dish culture medium. One of these, the Petrifilm™ system, comprising rehydratable nutrients, is very widely used. Another system developed by Nissui Pharmaceutical, Compact Dry™, also consists of a dehydrated medium. These culture media have the advantage that they can be preserved for longer than a ready-to-use agar culture medium. They may also, as is the case for Petrifilm™, be small in size and thus take up a small amount of incubation space.

Thus, broadly speaking, there are two ways to obtain a rehydratable culture medium: the first consists in placing the culture medium in liquid form in the support, then drying the whole thing, and
the second consists in adhering the culture medium in dehydrated form to a support, so as to immediately obtain a rehydratable culture medium.

The first method, namely obtaining rehydratable nutritive media manufactured including a phase for wet impregnation of the nutrients, has been the subject of several patent applications. Thus, patent application CN102337324 describes a method in which the nutritive broth is mixed with a chemical component which evaporates rapidly. Document WO2005/061013 describes a marker dissolved in a solvent and deposited on an absorbent layer, so as to detect vaginitis. More recently, patent application US20130089887 describes a support, namely a thin membrane impregnated with chromogenic and/or fluorogenic substrates dissolved in a solvent, placed in contact with an agar medium.

Nonetheless, this method for dissolving in water or in a solvent has a negative impact on the length of time for which the rehydratable culture medium can be preserved. Indeed, placing certain fragile products such as enzymes or enzymatic or metabolic substrates or antibiotics in suspension may have a severe impact on their overall stability. The heating required to dry the culture medium may also denature, and render ineffective, the heat-sensitive components of the reaction medium. This method in aqueous phase also does not make it possible to control and vary the location of the reaction medium and/or the various additives required for bacterial visualization.

In order to overcome the drawbacks of the culture media obtained by this method, the second method proposes placing the nutritive powder directly onto the support without a prior phase of dissolving said powder.

Thus, 3M propose a dehydrated nutritive medium coated with adhesive and placed on a film without having gone through a prior phase of dissolving the medium. This device consists of two parts, a bottom film and a top film, covered at their surface by certain components of the dehydrated culture medium. At the time of the analysis, the sample is placed between these two films.

This device and the associated detection method, as described in application WO 2009/082667, have several drawbacks.

First of all, this device requires, for its manufacture, a step of adhering the dehydrated nutrients to the films which have had to be coated with adhesive beforehand. Following this, the culture medium cannot de facto form a three-dimensional structure with variable height and layered concentrations, since it is adhered to a film. Only one small superficial layer of medium is therefore available. The volume of the liquid sample required for microbiological analysis may therefore not exceed 1 or 2 ml, which impacts the threshold for detection sensitivity. Then, the packaging of the Petrifilm™ requires the manufacturing of the bottom film and the top film together. It also does not make it possible to have several different culture media on the same device. Moreover, this device has limited applications and cannot, for example, be used for taking swabs or as a dressing. Finally, the Petrifilm™ necessarily requires the input of an external operator providing the aqueous sample.

On the other hand, in an earlier patent application FR1257047, the applicant proposes a method for isolation, from a sample to be analyzed, on a culture medium that is rehydratable in situ, which makes it possible to obtain isolated colonies. This rehydratable medium is covered with a membrane enabling colonies to be isolated. Thus, the culture medium remains sterile and the colonies develop on the membrane which is just above said medium.

However, isolation of colonies, on an agar or non-agar support, is sometimes seen as a constraint and is often incompatible with experiments carried out outside the laboratory and/or by people having little knowledge and know-how in the field of microbiology.

AIMS

In light of all the problems laid out above, the present invention proposes a novel method for detection, identification and enumeration of microorganisms liable to be contained in a sample.

Thus, one aim of the present invention is to provide a device comprising a dehydrated medium improving detection sensitivity.

Another aim of the present invention is to provide a method for detection, identification and enumeration of microorganisms without having to rely on isolation.

Another aim of the present invention is to provide a device and a method enabling multi-detection, and thus to obtain, from the same sample to be analyzed and without carrying out isolation, isolated, identifiable and countable cultures on different reaction media present on the same device.

One aim of the invention is also to provide a particularly flexible device and method. The reaction medium may be a more or less complex medium, which is chromogenic, for example, or may be very simple, that is to say solely containing a limited number of substrates (antibiotics, metabolic substrates, etc.). The device and the method may also have very varied modes of use, such as a swab, or an absorbent medium for visualizing microbial contaminations in dressings, sanitary pads or food packaging.

Another aim of the present invention is to provide a device which can be used by people having little know-how in microbiology. Thus, the device may be rehydrated in one go by the operator at the time of the analysis of the sample. Rehydration may also be carried out in situ without the input of the operator, especially if the sample to be tested is placed in proximity to the rehydratable reaction medium, allowing its gradual rehydration. The sample to be analyzed may for example be an exudative wound or a piece of meat and may produce a liquid liable to contain the microorganisms to be detected.

Another aim of the present invention is to provide a device which itself serves for the collection of the sample, such as a swab.

One aim of the present invention is to provide a device, the production and sale of which are facilitated by the fact that the porous support dry-impregnated by a reaction medium is produced independently of its packaging.

Another aim of the present invention is to provide a device in which a concentration gradient of the reaction substrates is created, thereby enabling the amount of these substrates to be limited, and the production cost of the device to be limited.

Other aims will become apparent upon reading the present application.

DETAILED DESCRIPTION

The present invention therefore aims to achieve all or some of the abovementioned aims.

Consequently, a subject of the present invention is a method for the detection and/or identification and/or enumeration of at least one target microorganism in a sample liable to contain it, comprising the following steps:
 (a) providing a device for the detection and/or identification and/or enumeration of microorganisms comprising a porous support comprising reaction medium powder throughout its thickness, said porous support having been dry-impregnated throughout its thickness by a dehydrated reaction medium,
 (b) placing a sample in contact with the porous support,
 (c) incubating the device,
 (d) detecting and/or identifying and/or enumerating the colony or colonies of microorganisms within the porous support, when the microorganisms sought are present in the sample.

According to the invention, the device is dry-impregnated throughout its thickness by a dehydrated reaction medium. The incorporation of pulverulent materials into porous supports may be carried out according to at least four techniques:
 use of a vacuum pump as described in U.S. Pat. No. 5,213,843;
 mechanically vibrating the porous support itself, on which the powder has been placed, by any vibrating system, the vibrations making it possible to cause the powder to penetrate more or less deeply;
 use of an electrostatic field;
 ultrasonic vibration, simultaneous to the application of the powder, using an ultrasound generator which causes a sonotrode to vibrate, as described in patent application FR 2866578. When the porous product passes under the sonotrode, the action of the latter vibrates the powder particles, and they then penetrate into the cavities of the porous substance.

Preferentially, the method for manufacturing the porous support dry-impregnated throughout its thickness comprises a step of vibrating the powder particles by means of an electric field. Preferentially, this is an alternating electric field. Patent EP 1.028.836 describes the impregnation of textiles (nonwoven, woven, etc.) by applying an alternating electric field between two systems of electrodes, between which the powder-covered textile is located. The powder particles, which become electrically charged, start to vibrate at the frequency of the alternating field. Thus, surprisingly, this technique may be used to dry-impregnate a porous support with a dehydrated reaction medium. The movements of the particles therefore enable their penetration into the pores of the support. The particles have penetrated the porous support at depth, throughout the thickness of the support.

Thus, the zones of the support that are impregnated with medium are impregnated throughout the thickness of the support, since the powder has passed through the thickness of the porous support. Thus, at least all or some of the porous support comprises a reaction medium in powder form throughout its thickness, with some zones on the support nonetheless being able to be devoid of any medium, such as for example the perimeter of the support.

The degree of impregnation of the particles through the thickness of the support may be controlled, for example homogeneously, in a localized manner or as a gradient, depending on the characteristics of the materials present (supports and powders), but also the characteristics of the method employed (intensity of the electric field, treatment time, frequency, etc.).

The support may be impregnated sequentially over time, which enables better impregnation. Thus, the impregnation with gelling agent may take place before the impregnation with reaction medium.

Dry impregnation of a dehydrated medium throughout the thickness of a porous support does not require the use of water and enables the location of the particles to be controlled. Moreover, it enables flexibility through the thickness of the impregnated layer by enabling different zones to be defined through the thickness, which are in different amounts and are of different natures.

Advantageously, a concentration gradient of the reaction substrates is created in the porous support, thereby making it possible to limit the amount of these substrates and to limit the production cost of the device. It may also be chosen to have a porous support comprising one type of substrate distributed homogeneously and another type of substrate distributed in a gradient. Advantageously, the support is impregnated throughout its thickness by a nutritive medium and superficially by chromogenic substrates. In another embodiment, the substrates are encapsulated, enabling their sequential release after incubation of the device. Thus, this embodiment has the advantage of limiting the use of the substrates by avoiding their dilution in the nutritional medium during rehydration of the medium.

Similarly, a selective agent such as an antibiotic may also be encapsulated. This embodiment is particularly advantageous since it makes it possible to postpone placing the contents (comprising a small amount of target microorganisms, if the latter are present) in contact with the selective agent intended to orient the growth of the microorganisms toward that of the microorganisms being sought. Thus, the microorganisms in the microbial stress phase are not directly placed in contact with the selective agent, the latter carrying a risk, at this stage, of either slowing down the growth of said microorganisms and hence increasing the time needed for analysis, or of completely inhibiting the growth of said microorganisms and thus preventing their detection/identification. This is because the target microorganisms are said to be "stressed" when they are present in the sample to be analyzed. The microorganisms (including the target microorganisms) need a certain amount of time to adapt to the conditions existing within the porous support. In their "stressed" state, the target microorganisms are particularly sensitive, especially to the presence of selective agents such as antibiotics.

Thus, the porous support may comprise different reaction media. These reaction media are located in different zones of the support. These zones may correspond to vertical zones and therefore to the thickness of the support, and/or correspond to horizontal zones of the support. The porous support may therefore have, in one zone, several reaction media, such as for example a culture medium and a visualization medium. The device may also have one or more reaction media arranged in different zones of one or more porous supports, each of these zones having reaction medium distributed throughout the thickness of the support.

In practice, several parameters may influence carrying out this method, such as, principally:
the texture of the network of fibers or filaments, or generally speaking of the porous support used;
the physicochemical properties of the powders, such as the nature or the particle size of the powder;
the duration of the treatment, the intensity of the electric field and also the frequency of the electric field.

It will therefore be necessary to adapt these parameters so as to enable satisfactory dry impregnation of the reaction medium in the porous support.

Preferentially, the amount of reaction medium, in powder form, impregnated in the porous support is between 0.01 g/cm$^3$ and 0.1 g/cm$^3$, preferably between 0.02 g/cm$^3$ and 0.09 g/cm$^3$, more preferentially between 0.03 g/cm$^3$ and 0.06 g/cm$^3$.

Preferentially, when the reaction medium comprises a culture medium and optionally a visualization medium, the amount of impregnated reaction medium, in powder form, is between 0.01 g/cm$^3$ and 0.09 g/cm$^3$, more preferentially between 0.03 g/cm$^3$ and 0.06 g/cm$^3$. Thus, an advantage of the present invention is to enable optimized growth, especially due to the excess amount of culture medium which thereby alleviates problems of nutrient competition among the microorganisms.

Preferentially, when the reaction medium comprises a visualization medium without culture medium, the amount of impregnated reaction medium, in powder form, is much lower and is between 0.10 mg/cm$^3$ and 10 mg/cm$^3$.

According to the invention, the porous support is placed in contact with the sample.

In one embodiment of the invention, the sample is aqueous and will enable rehydration of the reaction medium contained in the porous support.

According to another embodiment, a suitable volume of liquid is added to the sample and/or to the porous support in order to rehydrate the reaction medium, when the sample is not aqueous or is insufficiently aqueous.

In practice, those skilled in the art will choose the suitable volume of liquid or of aqueous sample as a function of its viscosity and of the diameter of the porous support, so as to rehydrate the medium and enable the growth of the microorganisms.

Advantageously, the rehydration of the porous support requires a volume of liquid or of aqueous sample of greater than 2 ml, preferentially greater than 3 ml, even more preferentially greater than 4 ml, which makes it possible to improve detection sensitivity when the microorganisms are at a low concentration in the sample.

According to the present invention, the sample may comprise a prior step of preparation, concentration or dilution of the sample.

According to the invention, rehydration of the support may be carried out with or without operator intervention.

The aqueous sample may be added manually by means of a pipette or automatically into the device. It may also be contained in at least one reservoir integrated into the device and/or in channels enabling rehydration of the porous support. It then spreads through the support simply by pressing on the reservoir.

Advantageously, the sample is placed in contact with the porous support by placing it under the porous support. Thus, rehydration takes place via the lower and/or lateral portion, preferably via the lower portion. This operating procedure enables homogeneous hydration of the whole porous support and especially avoids nutrients and/or substrates from being drawn, by the liquid or the aqueous sample, into the lower portion of the device. Advantageously, this operating procedure enables the method according to the invention to be carried out in space by solving the problem linked to the absence of gravity for the sample and/or the liquid.

In one embodiment, there is no human intervention and the aqueous sample originates directly from a zone producing the liquid to be tested. This may be, for example, an exudative wound or foodstuffs which release liquids during their storage. The sample, by its very nature, will release some of its constituent liquids which will, over time, soak into the porous support. The zone producing the sample to be tested may also be a perineal zone of humans or animals excreting urine. The porous support is then placed in proximity to this zone and is impregnated gradually by the aqueous sample produced. In another embodiment, the sample is placed in contact with the porous support by taking the sample using the porous support. The porous support is thus used as a swab and the operator must place the latter in a tube containing a suitable amount of liquid if the sample is not aqueous or is insufficiently aqueous.

The device is subsequently incubated in situ (in the case of dressings, sanitary pads, etc.) or in an incubator for a sufficient length of time to enable the detection of microbial colonies within the porous support.

According to one preferred embodiment, the method according to the invention is a detection method which may be carried out by visual or optical reading of the porous support.

The invention also relates to a device comprising a porous support dry-impregnated throughout its thickness with a dehydrated reaction medium enabling the visualization of colonies of microorganisms within said support, said porous support being calendered.

The porous support has been dry-impregnated throughout its thickness, that is to say that when a reaction medium is present at a location of the support, it is present in this zone throughout the thickness of the support.

The porous support has undergone a calendering operation. Calendering, through the pressure and heating temperature generated, enables stable maintenance and retention over time of the dehydrated reaction medium in the porous support by ensuring the retention of the different elements such as nutritive elements in the porous support. It also makes it possible to obtain a completely smooth and planar upper surface of the porous support.

Preferentially, calendering is carried out at a temperature higher than room temperature, preferentially at a temperature of between 30° C. and 60° C. A temperature of lower than 60° C. avoids denaturing the thermolabile components.

Aside from accelerating rehydration of the porous support compared to a non-calendered porous support, calendering enables compression of the fibers constituting the porous support. This compression, combined with the presence of the dehydrated medium within the porous support, enables simultaneous rehydration throughout all the zones of the support which are placed horizontally, and thus preserves the chosen distribution (homogeneous or in a gradient) of the substances.

Calendering thus makes it possible to keep the reaction medium within the support and enables easy handling thereof.

The support comprises at least one dehydrated reaction medium in powder form distributed throughout the thickness of the porous support, said porous support having a thickness of between 0.5 and 2 mm after calendering. Preferentially, the porous support has a thickness of from 0.8 mm to 1.8 mm, even more preferentially still from 1 to 1.5 mm. The surface area of the porous support is between 1 $cm^2$ and 40 $cm^2$, preferentially between 10 $cm^2$ and 30 $cm^2$, more preferentially between 15 $cm^2$ and 25 $cm^2$.

The porous support is able to retain a volume of water greater than 2 ml, preferentially greater than 3 ml. Thus, a porous support with a surface area of 25 $cm^2$ and a thickness of 1 mm after calendering will be able to retain a volume of water of 3 ml.

The device according to the invention, through the presence of culture medium throughout its thickness, therefore has the advantage of enabling improved sensitivity through its ability to retain a high volume of liquid sample.

Preferentially, the amount of reaction medium in powder form impregnated in the porous support is between 0.01 $g/cm^3$ and 0.1 $g/cm^3$, preferably between 0.01 $g/cm^3$ and 0.09 $g/cm^3$, more preferentially between 0.03 $g/cm^3$ and 0.06 $g/cm^3$. Preferentially, when the reaction medium comprises a culture medium and optionally a visualization medium, the amount of reaction medium in impregnated powder form is between 0.01 $g/cm^3$ and 0.09 $g/cm^3$, more preferentially between 0.03 $g/cm^3$ and 0.06 $g/cm^3$. Thus, an advantage of the present invention is to enable optimized growth, especially due to the excess amount of culture medium which thereby alleviates problems of nutrient competition among the microorganisms. Surprisingly, detection of certain strains is thus faster than on agar medium.

Preferentially, the device according to the invention comprises at least one antibiotic and/or at least one heat-sensitive compound such as an enzymatic or metabolic substrate. It thus has the advantage of having enhanced stability due to the fact that this compound was not placed in suspension during the manufacture of the device and/or did not undergo the heating needed to dehydrate a culture medium.

According to one embodiment, the device comprises a porous support comprising at least one reaction medium in powder form homogeneously distributed through the thickness of the porous support. According to another embodiment, at least one reaction medium in powder form is distributed in a graduated manner through the thickness of the porous support.

Another embodiment proposes at least two different reaction media in powder form distributed in at least two layers, said support comprising, at a given point through the thickness, one and/or the other culture medium.

According to the invention, the device comprises a plurality of reaction media.

Preferentially, the device comprises an upper protection layer. The protection layer is arranged on the porous support and no other layer is arranged between the porous support and the protection layer. Preferably, the protection layer is placed directly on the porous support.

The protection layer may be translucent or transparent, enabling colonies to be viewed through this layer. It also makes it possible to avoid contaminations during incubation. It is impermeable to bacteria and limits the loss of water vapor. Indeed, the device is incubated for a predetermined period of time and at a predetermined temperature, enabling growth of the microorganisms independently of the ambient moisture conditions. Thus, the nature of the upper layer is chosen so as to enable the gas exchanges necessary for the growth of the microorganisms, while enabling local hydration.

Preferentially, the device comprises a receptacle for containing the aqueous sample and/or the liquid. Preferably, the receptacle also comprises the porous support which is then preferentially rehydrated through its lower portion.

Advantageously, the device comprises a lower, waterproof, layer. Preferably, this lower layer is rigid, enabling better handling of the device. It is manufactured from compounds such as polyester, polypropylene and polystyrene. Preferably, it is manufactured from cellulose. It may be cardboard or paper combined with a waterproof film. It may contain thermo-formed channels which will serve for the proper rehydration of the porous support.

Advantageously, the different layers of the device are manufactured from recyclable materials.

According to one particular embodiment of the invention, the lower layer is translucent or transparent.

According to one particular embodiment of the invention, the device also comprises an identification code such as bar codes or RFID tags.

According to the present invention, it is also possible to combine, within the same device, different reaction media arranged alongside one another which will be rehydrated simultaneously with the same sample to be tested.

In one embodiment, the device comprises a rod, at the end of which the porous support, dry-impregnated by a dehydrated reaction medium, is fixed.

The fixing may be carried out by any means known to those skilled in the art, such as, for example, adhesive bonding or else heat sealing.

The porous support fixed to a rod may thus act as a swab.

Advantageously, the device also comprises a waterproof transparent tube which may receive the swab, and a hermetic cap for the tube.

After taking the sample using the swab, the latter is placed in the tube which contains the water necessary to rehydrate the porous support placed in its apical portion. The tube is then capped and incubated.

In another embodiment, the porous support is integrated into a dressing, a bandage, a sanitary pad or an item of food packaging.

Preferentially, the device comprises, under the porous support, a lower, porous, layer which is placed in contact with the sample to be analyzed.

Even more preferentially still, the device also comprises an upper, transparent and impermeable, layer over at least a portion.

The invention also relates to the use of a device according to the invention for detecting and/or identifying and/or enumerating at least one target microorganism in a sample liable to contain it.

Advantageously, the invention relates to the use of a device comprising a rod, at the end of which said porous support is fixed, as a swab.

In another embodiment, the invention relates to the use of a device according to the invention as a dressing.

According to another embodiment, the invention also relates to the use of a device according to the invention as a sanitary pad.

In yet another embodiment, the invention relates to the use of a device according to the invention as packaging for foodstuffs.

The term "sample" is intended to mean a small portion or small amount separated from an entity by a subtractive act usually called sampling, for purposes of analysis. The sample may be of biological, human, animal, vegetable or environmental origin. It may relate to a product in the course of an industrial process or a finished product, for example a food product. It may therefore correspond to a sample of biological fluid (whole blood, serum, plasma, urine, cerebrospinal fluid, organic secretion), a tissue sample or isolated cells. It may be of industrial origin, i.e., according to a nonexhaustive list, a sample of air, a sample of water, a sample taken from a surface, a piece or a product in the course of treatment or manufacture, a product of food origin. Among samples of food origin, mention may be made nonexhaustively of a sample from milk products (yoghurts, cheeses, etc.), meat, fish, eggs, fruits, vegetables, water, drinks (milk, fruit juices, soda, etc.) and the constituent or ancillary products of the finished product. A food sample may finally be obtained from feed intended for animals, such as especially meal as animal feed. Before being analyzed, this sample may undergo preparation such as enrichment, extraction, concentration, purification, by methods known to those skilled in the art.

Within the context of the present invention, the term "microorganism" covers Gram-positive or Gram-negative bacteria, yeasts, molds, amoebae and, more generally, unicellular organisms, invisible to the naked eye, which can be handled and multiplied in the laboratory.

According to a preferred embodiment of the invention, the microorganism is a Gram-negative or Gram-positive bacterium, or a yeast.

By way of Gram-positive bacteria, mention may be made of the bacteria of the following genera: *Enterococcus, Streptococcus, Lactobacillus, Bifidobacterium, Staphylococcus, Bacillus, Listeria, Clostridium, Mycobacteria, Nocardia, Corynebacteria, Micrococcus* and *Deinococcus*.

By way of Gram-negative bacteria, mention may be made of the bacteria of the following genera: *Salmonella, Escherichia coli* and *Pseudomonas*.

By way of yeasts, mention may be made of the yeasts of the following genera: *Candida, Cryptococcus, Saccharomyces* and *Trichosporon*.

By way of molds, mention may be made of the molds of the following genera: *Aspergillus, Penicillium, Cladosporium*.

The term "porous support" is intended to mean a volume with adapted porosity, in the form of fabric or nonwoven, having a fibrous or filamentous network of open-pore foam. This is a three-dimensional support, in which the particles of the reaction medium have penetrated, in a given zone of the porous support, throughout its thickness.

The support may be based on various absorbent compounds with a very high water retention capacity, such as viscose, rayon, cotton, natural cellulose fibers or chemically modified cellulose fibers such as carboxymethyl cellulose, absorbent or superabsorbent chemical polymers such as polyacrylate salts or acrylate/acrylamide copolymers. Preferentially, the porous support will have a basis weight of between 50 g/m$^2$ and 150 g/m$^2$, preferentially between 90 g/m$^2$ and 110 g/m$^2$.

The term "reaction medium" is intended to mean a medium comprising all the elements needed for the survival and/or growth of the microorganisms. This reaction medium may either serve solely as visualization medium, or serve as culture medium and visualization medium. In the first case, culture of the microorganisms takes place beforehand, and in the second case, the reaction medium is also the culture medium. Thus, the reaction medium of the device according to the invention is a visualization medium and/or a culture medium.

The term "visualization medium" is intended to mean any medium containing a molecule able to couple with the microorganisms or the binding partners of said microorganisms and enabling, through their transduction properties (fluorescence, coloring, radioactivity, etc.), visualization of the presence of said microorganisms. This visualization of the presence of the target microorganisms may especially be obtained by viewing (with the naked eye) or optical reading of coloring or fluorescence over all or a portion of the support.

The term "culture medium" is intended to mean a medium comprising all the elements needed for the survival and/or growth of the microorganisms. In practice, those skilled in the art will choose the culture medium as a function of the target microorganisms, according to criteria perfectly well-known and within the scope of these people skilled in the art.

The reaction medium according to the invention may contain optional additives such as, for example: peptones, one or more growth factors, carbohydrates, one or more selective agents, buffers, dyes, one or more gelling agents, hydrogels, viscous agents, etc.

Preferentially, the reaction medium of the device according to the invention comprises at least one gelling agent, the amount of which is between 1 mg/cm$^2$ and 2 mg/cm$^2$. The gelling agent may be chosen from the gelling agents well-known to those skilled in the art, such as agar, agarose, poloxamers, guar gum or xanthan.

Thus, the porous support and the gelling agents make it possible to limit the diffusion of the substrates and microorganisms, and participate in the formation of isolated microbial colonies.

The term "powder" is intended to mean particles having a particle size of from 1 to 200 micrometers. Micronization of the minority compounds such as the substrates and antibiotics is possible, to perfect the homogenization of the powder.

Within the context of the present invention, "at least one target microorganism" is intended to mean at least one microorganism which it is desired to detect and/or identify and/or count.

Within the context of the present invention, the definition of "detection sensitivity" is identical to that which is commonly accepted in the prior art, namely the ability to give a positive result (appearance of a colored and/or fluorescent reaction) when the target bacterial strain is present in the sample.

BRIEF DESCRIPTION OF THE DRAWINGS

FIG. 1 is an entirely nonlimiting schematic representation of the invention.

Figure 1A:
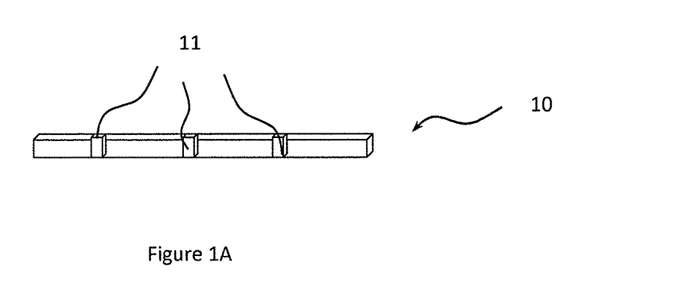

FIG. 1 schematically represents a porous support (10) contained in a device according to the invention comprising a plurality of reaction media (11) at different zones, each of these zones then having reaction medium distributed throughout the thickness of the support.

Figure 1B:
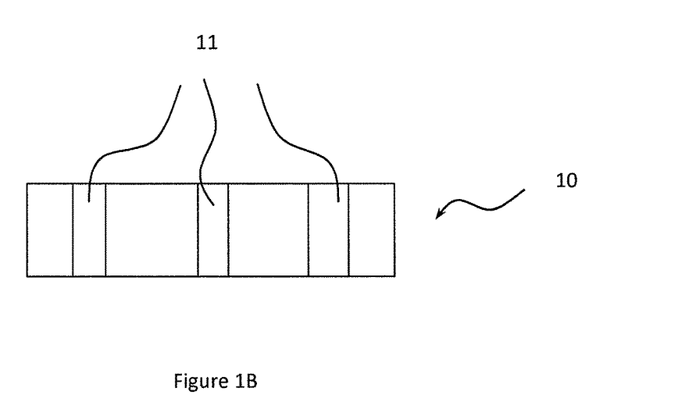

FIG. 1b corresponds to a plan view of the porous support (10) according to the invention.

Figure 1C:
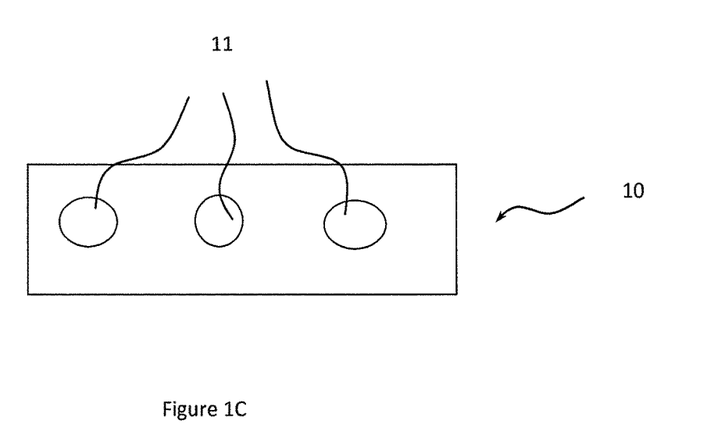

FIG. 1c corresponds to a plan view according to another embodiment in which the porous support is impregnated by reaction media at zones forming circles on the surface, each of these zones then having reaction medium distributed throughout the thickness of the support.

EXAMPLES

Examples 1 preparation of a porous support according to the invention, comprising powder of culture medium distributed homogeneously within the support
Material:
 95 g/m² nonwoven supports (ref: 95NN81, SCA Life) 25 cm² in size and 2 mm thick (before calendering):
 0.13 g of ChromID CPS 3 dehydrated culture medium (600-04595, bioMérieux)+0.06 g xanthan (ref: 4452073479, Alliance gum)
Protocol:
 0.2 g of powder is sprinkled homogeneously onto the support then the support is placed between two electrodes with application of a voltage of 3200 V/mm for 15 seconds at a relative humidity of between 35 and 45%.

The support is calendered at 60° C. by applying a pressure of $3 \times 10^5$ Pa/cm².

The supports are thus passed through by the powder of culture medium.

Example 2 preparation of a porous support according to the invention, comprising reaction medium powder distributed homogeneously within the support and reaction medium powder distributed solely at the surface
Material:
 95 g/m² nonwoven supports 25 cm² in size and 2 mm thick (before calendering) (ref: 95NN81, SCA Life)
 Medium 1: ChromID CPS 3 dehydrated culture medium (0.13 g) (600-04595, bioMérieux)+0.06 g xanthan (ref: 4452073479, Alliance gum)
 Medium 2: ChromID CPS 3 dehydrated culture medium (0.13 g) (600-04595, bioMérieux)+0.06 g xanthan (ref: 4452073479, Alliance gum)+micronized imipenem monohydrate (sp2129, Merck and Co)

A first face is impregnated with reaction medium homogeneously according to the protocol of example 1. Then, the support is turned over and the second face is impregnated with a reaction medium comprising an antibiotic, imipenem, by means of an electric field weaker than 1050 V/mm for 15 seconds, so that the powder penetrates less and remains more on the surface. Calendering is carried out as described in example 1.

Example 3 preparation of a porous support according to the invention, comprising reaction medium powder distributed homogeneously within the support and reaction medium powder distributed in a gradient within the support Material: identical to example 2.

A first face is impregnated homogeneously with medium 1 according to the protocol of example 1. Then, the support is turned over, and the second face is impregnated with the second medium with the same strong electric field (3169V/mm).

An impregnation gradient of the second reaction medium within a homogeneous distribution of the first reaction medium is therefore obtained.

Example 4 preparation of a porous support according to the invention, comprising different reaction media distributed within the support in two layers A first face is impregnated homogeneously with the reaction medium with an intermediate electric field (1408 V/mm). Then, the support is turned over and the second face is impregnated with a second reaction medium with the same intermediate electric field (1408 V/mm).

Two separate layers of reaction media are therefore obtained, and the whole thickness of the porous support comprises reaction medium powder.

Example 5

Detection of *Escherichia coli* and *Pseudomonas aeruginosa* with a device according to the invention comprising 1 mg/l imipenem as antibiotic
Material:
 1. Reagents Used
  CPS3 agar (bioMérieux, ref: 43549, 22002)
  Chrom ID CPS3 dry medium (bioMérieux, ref: 600-04595)
  Tryptone salt 9 ml vial, (AES, ref: 111499, batch 327601)
  Xanthan (Alliance Gum FF Pharma, batch FF 2524429), particle size<75 μm.
  Imipenem (bioMérieux INC, ref: 066259-1)
 2. Strains Used
  *E. coli* ATCC 25922, MIC (minimum inhibitory concentration) of 0.12 mg/ml
  *Pseudomonas aeruginosa* ATCC 27853, MIC 2 mg/ml
Method:
 To produce the agar media, a liter of water is added to the test specimen of the dry medium, i.e. 38.3 g for ChromID CPS3. The dry medium is then dissolved with stirring, brought to the boil then sterilized by autoclaving. After cooling the agar medium to 55° C., the imipenem sterilized by filtration is added at a concentration of 1 mg/l. To carry out impregnation according to the present invention of the dry medium Chrom ID CPS3, a test specimen of the dry medium corresponding to the manufacture of one liter of medium is taken, i.e. 26 g, to which test specimen xanthan (20 g) and imipenem (1 g) are added. All the constituents are then mixed together in a Turbula®. The porous supports are then impregnated by the culture media powder produced as described above and sterilized by gamma radiation between 10 and 17 kGy.

Results:
ChromID CPS3 agar

|  | Starting concentrations | ChromID CPS3 without antibiotic | | ChromID CPS3 with 1 mg/l imipenem | |
| --- | --- | --- | --- | --- | --- |
|  | CFU/ml | CFU | CFU/ml | CFU | CFU/ml |
| *E. coli* ATCC 25922 | $10^3$ $10^5$ | 67/56/88 ≥300 colonies | 703 — | 0/0/0 0/0/0 | 0 0 |
| *Pseudomonas aeruginosa* ATCC 27853 | $10^3$ $10^5$ | 122/105/105 ≥300 colonies | 1107 — | 69/61/73 ≥300 colonies | 677 — |

CFU: Colony Forming Unit

Porous Support According to the Invention

|  | Starting concentrations | ChromID CPS3 without antibiotic | | ChromID CPS3 with 1 mg/l imipenem | |
| --- | --- | --- | --- | --- | --- |
|  | CFU/ml | CFU | CFU/ml | CFU | CFU/ml |
| *E. coli* ATCC 25922 | $10^3$ $10^5$ | 28/32/32 ≥300 colonies | 307 — | 0/0/0/0/0 0/0/0/0/0 | 0 0 |
| *Pseudomonas aeruginosa* ATCC 27853 | $10^3$ $10^5$ | 49/57/61 ≥300 colonies | 556 — | 40/53/38/39/46/56 ≥300 colonies | 453 — |

Conclusion

Two strains were tested: *E. coli* ATCC 25922 (MIC 0.12) and *Pseudomonas aeruginosa* ATCC 27853 (MIC 2 mg/l).

The results obtained with the porous supports according to the invention and with the ChromID CPS3 agar media are consistent with the growth of the *Pseudomonas aeruginosa* ATCC 27853 strain having an MIC of 2 mg/l in the presence of 1 mg/l imipenem and with the absence of growth of the *E. coli* ATCC 25922 strain having an MIC of 0.12 mg/l in the presence of 1 mg/l imipenem.

Example 6

Detection of *Proteus* and of *Pseudomonas* with a device according to the invention comprising 1.5 mg/l ciprofloxacin as antibiotic Material:
  Mueller Hinton 2 powder base (bioMérieux, ref: 8301143, batch 1002661760)
  American Agar (ROKO SA, ref: 11000301)
  European Agar (SETEXAM, ref: TMN2)
  Ciprofloxacin (HCL TOKU-E COMPANY, ref: C032)
  ChromID CPS3 agar (bioMérieux, ref: 43549, 22002)
  Chrom ID CPS3 dry medium (bioMérieux, ref: 600-04595)
  Tryptone salt 9 ml vial (AES, ref: 111499, batch 327601)
  Pre-cast MH2 (Muller Hinton 2) agar (bioMérieux, ref: 43301)
  TSA agar (bioMérieux, ref: 43011)
  Xanthan (Alliance Gum FF Pharma, batch FF 2524429), particle size<75 µm
  Ciprofloxacin (HCL, ref: 00743041)

The porous supports were impregnated by the following media:
  MH2 (Muller Hinton 2)+xanthan alliance gum pharma
  MH2+xanthan alliance gum pharma+1.5 mg/l ciprofloxacin
  MH2+xanthan alliance gum pharma
  CPS3+xanthan alliance gum pharma
  CPS3+xanthan alliance gum pharma+1.5 mg/l ciprofloxacin Strains Tested:
  *Proteus mirabilis* API 8803099, ADM AP3, MIC: 0.125
  *Proteus mirabilis* API 8803080, ADM JS10, MIC: 0.25
  *Proteus mirabilis* API 9406037, bioMérieux collection, MIC: 4
  *Proteus vulgaris* API 8803017, ADM CQ11, MIC: 0.125
  *Pseudomonas aeruginosa* API 9405061, bioMérieux collection, MIC: 0.125
  *Pseudomonas aeruginosa* API 7509005, ATCC 25853, MIC: 0.5
  *Pseudomonas aeruginosa* API 9410075, MIC: 16
  *Pseudomonas aeruginosa* API 9405063, MIC: 4

Method:

To produce the agar media, a liter of water is added to the test specimen of the dry medium, i.e. 38.3 g for ChromID CPS3 and 41.57 g for the Muller Hinton 2 medium. The dry medium is then dissolved with magnetic stirring, brought to the boil then sterilized by autoclaving. After cooling the agar medium to 55° C., the ciprofloxacin sterilized by filtration is added to the agar medium at a concentration of 1.5 mg/l. To carry out impregnation according to the present invention of the dry media MH2 and Chrom ID CPS3, a test specimen of the dry medium corresponding to the manufacture of one liter of medium is taken, i.e. 26 g for Chrom ID CPS3 and 26.07 g for the Muller Hinton 2 medium, to which test specimen xanthan (20 g) and, if appropriate, ciprofloxacin (1.5 g) are added. The whole thing is then mixed together in a Turbula®. The porous supports are then impregnated with the culture media powders as described above and sterilized by gamma radiation between 10 and 17 kGy.

Results:

| STRAINS | MIC | MH2 Agar medium | MH2 Agar medium + 1.5 mg/l Ci | Impregnation of porous support with MH2 | Impregnation of porous support with MH2 + 1.5 mg/l Ci |
| --- | --- | --- | --- | --- | --- |
| *Proteus mirabilis* API 8803099 | 0.032 | ++ | -- | ++ | -- |
| *Proteus mirabilis* API 8803080 | 0.38-0.5 | ++ | -- | ++ | -- |
| *Proteus mirabilis* API 9406037 | 8-12 | ++ | ++ | ++ | ++ |
| *Proteus vulgaris* API 8803017 | 0.125 | ++ | -- | ++ | -- |
| *P. aeruginosa* API 9405061 | 0.25 | ++ | -- | ++ | -- |

-continued

| STRAINS | MIC | MH2 Agar medium | MH2 Agar medium + 1.5 mg/l Ci | Impregnation of porous support with MH2 | Impregnation of porous support with MH2 + 1.5 mg/l Ci |
|---|---|---|---|---|---|
| *P. aeruginosa* API 7509005 | 0.25 | ++ | -- | ++ | -- |
| *P. aeruginosa* API 9410075 | >32 | ++ | ++ | ++ | ++ |
| *P. aeruginosa* API 9405063 | 6-8 | ++ | ++ | ++ | ++ |

| STRAINS | MIC | ChromID CPS3 Agar medium | ChromID CPS3 Agar medium + 1.5 mg/l Ci | Impregnation of porous support with ChromID CPS3 | Impregnation of porous support with ChromID CPS3 + 1.5 mg/l Ci |
|---|---|---|---|---|---|
| *Proteus mirabilis* API 8803099 | 0.032 | ++ | -- | ++ | -- |
| *Proteus mirabilis* API 8803080 | 0.38-0.5 | ++ | -- | ++ | -- |
| *Proteus mirabilis* API 9406037 | 8-12 | ++ | ++ | ++ | ++ |
| *Proteus vulgaris* API 8803017 | 0.125 | ++ | -- | ++ | -- |
| *P. aeruginosa* API 9405061 | 0.25 | ++ | -- | ++ | -- |
| *P. aeruginosa* API 7509005 | 0.25 | ++ | -- | ++ | -- |
| *P. aeruginosa* API 9410075 | >32 | ++ | ++ | ++ | ++ |
| *P. aeruginosa* API 9405063 | 6-8 | ++ | ++ | ++ | ++ |

CONCLUSION

In this example, the Muller Hinton and ChromID CPS3 agar media with or without 1.5 g/l ciprofloxacin were compared to the porous supports according to the present invention impregnated with the same media with or without 1.5 g/l ciprofloxacin for three strains of *Proteus mirabilis*, one strain of *Proteus vulgaris* and four strains of *Pseudomonas aeruginosa*. All these strains had an MIC around the value of 1.5 mg/l of ciprofloxacin. The strains with an MIC of less than 1.5 mg/l (*Proteus mirabilis*: API 8803099, *Proteus mirabilis*: API 8803080, *Proteus vulgaris*: API 8803017, *Pseudomonas aeruginosa*: API 9405061, *Pseudomonas aeruginosa*: API 7509005) do not grow on MH2 agar media+substrates+ciprofloxacin (1.5 mg/l) and ChromID CPS3 with ciprofloxacin added (1.5 mg/l). Similarly, these "ciprofloxacin-sensitive" strains, for an MIC of 1.5 mg/l, do not grow either on the porous supports impregnated with ChromID CPS3 media and MH2+substrate in the presence of 1.5 mg/l ciprofloxacin. The results obtained on agar media and on porous supports impregnated according to the present invention are therefore consistent with one another. All these strains grow on MH2+substrate or ChromID CPS3 agar media and on porous supports impregnated by MH2+substrate and ChromID CPS3 media.

The strains with an MIC of greater than 1.5 mg/l (*Proteus mirabilis*: API 9406037, *Pseudomonas aeruginosa*: API 9410075, *Pseudomonas aeruginosa*: API 940506) grow on all the agar or impregnated media, with or without ciprofloxacin (1.5 g/l). These results confirm that it is possible to produce culture media according to the present invention containing small amounts of active agents such as chromogenic substrates or antibiotics.

The invention claimed is:

1. A device comprising a porous support comprising at least one dehydrated reaction medium in powder form distributed throughout the thickness of the porous support, wherein the reaction medium is a visualization medium and/or a culture medium and said porous support has a thickness of between 0.5 and 2 mm and is calendered.

2. The device as claimed in claim 1, wherein the reaction medium in powder form is homogeneously distributed through the thickness of the porous support.

3. The device as claimed in claim 1, wherein the reaction medium in powder form is distributed in a graduated manner through the thickness of the porous support.

4. The device as claimed in claim 1, wherein at least two different reaction media in powder form are distributed in at least two layers, said porous support comprising, at a given point through the thickness, one of the reaction media.

5. The device as claimed in claim 1, wherein the reaction medium is a culture medium.

6. The device as claimed in claim 1, wherein the reaction medium comprises at least one gelling agent, the amount of which is between 1 mg/cm$^2$ and 2 mg/cm$^2$.

7. The device as claimed in claim 1, wherein the amount of reaction medium impregnated in the porous support is between 0.10 mg/cm$^3$ and 0.1 g/cm$^3$.

8. The device as claimed in claim 1, comprising a plurality of the porous supports.

9. The device as claimed in claim 1, wherein the porous support is integrated into a dressing, a bandage, a sanitary pad or an item of food packaging.

10. The device as claimed in claim 1, further comprising a rod including an end at which said porous support is fixed.

11. The device as claimed in claim 1, wherein the reaction medium is a culture medium for detecting a methicillin-resistant *Staphylococcus*.

12. The device as claimed in claim 1, wherein the thickness of the porous support is between 0.8 and 2 mm.

13. The device as claimed in claim 1, further comprising:
   an upper layer that is translucent or transparent and impermeable to bacteria; and
   a lower layer including channels or pores,
   wherein the porous support is between the upper and lower layers.

14. The device as claimed in claim 1, wherein the porous support further comprises an encapsulated chromogenic substrate or selective agent.

15. The device as claimed in claim 1, wherein the porous support further comprises a chromogenic substrate.

16. A device comprising:
   a powder having a particle size from 1 to 200 μm that comprises at least one dehydrated reaction medium including elements for survival and/or growth of a microorganism; and
   a calendered porous support having a thickness between 0.5 and 2 mm that is dry-impregnated with the dehydrated reaction medium throughout the thickness in an amount between 0.10 mg/cm$^3$ and 10 mg/cm$^3$ or between 0.01 g/cm$^3$ and 0.1 g/cm$^3$,
   wherein the porous support has a basis weight between 50 g/m$^2$ and 150 g/m$^2$ and a surface area between 1 cm$^2$ and 40 cm$^2$, and the porous support is able to retain a volume of water greater than 2 ml.

17. A method for the detection and/or identification and/or enumeration of at least one target microorganism in a sample liable to contain it, comprising the following steps:
   (a) providing the device as claimed in claim 1,
   (b) placing the sample in contact with the porous support of the device,
   (c) incubating the device, and
   (d) detecting and/or identifying and/or enumerating a colony or colonies of at least one target microorganism within the porous support when the target microorganism was present in the sample.

18. The method as claimed in claim 17, further comprising preparation, dilution or concentration of the sample prior to placing the sample in contact with the porous support.

19. The method as claimed in claim 17, wherein step b) is carried out by placing the sample under the porous support.

20. The method as claimed in claim 17, wherein step b) is carried out by taking the sample using the porous support.

21. The method as claimed in claim 17, wherein, when the sample is not aqueous or is insufficiently aqueous, a suitable volume of liquid is added to the sample and/or to the porous support in order to rehydrate the reaction medium.

* * * * *